United States Patent [19]
Yukl

[11] Patent Number: 6,057,761
[45] Date of Patent: May 2, 2000

[54] SECURITY SYSTEM AND METHOD

[75] Inventor: Tex Yukl, Juliaetta, Id.

[73] Assignee: Spatial Dynamics, Ltd., Clarkston, Wash.

[21] Appl. No.: 09/010,275

[22] Filed: Jan. 21, 1998

Related U.S. Application Data

[60] Provisional application No. 60/035,668, Jan. 21, 1997.

[51] Int. Cl.[7] .................................................. G08B 21/00
[52] U.S. Cl. .................................... 340/568.1; 250/358.1; 250/393; 340/540; 340/691.6; 345/208; 382/100; 382/325
[58] Field of Search ................................ 340/540, 568.1, 340/573.1, 674, 691.6, 693.6; 345/208; 382/100, 325; 250/358.1, 393

[56] References Cited

U.S. PATENT DOCUMENTS

| | | | |
|---|---|---|---|
| 4,234,844 | 11/1980 | Yukl | 324/642 |
| 4,318,108 | 3/1982 | Yukl | 343/753 |
| 4,878,059 | 10/1989 | Yukl | 343/753 |
| 4,947,848 | 8/1990 | Yukl | 600/398 |
| 4,949,094 | 8/1990 | Yukl | 343/785 |
| 4,975,968 | 12/1990 | Yukl | 118/708 |
| 5,181,234 | 1/1993 | Smith | 382/100 |

*Primary Examiner*—Glen Swann
*Attorney, Agent, or Firm*—Kolisch, Hartwell, Dickinson, McCormack & Heuser

[57] ABSTRACT

A microwave/dielectric-response-based security system, and a related methodology, for detecting contraband. The system (which implements the associated method) includes an interrogation region through which a target that is to be screened passes, an appropriate transmitter/receiver array that operates adjacent this region for illuminating, and monitoring a dielectric response received from, a target in the region, and electronics which effectively produce output data that is interpretable to identify the presence or absence of contraband associated with the illuminated target.

20 Claims, 7 Drawing Sheets

SECURITY SYSTEM AND METHOD

CROSS REFERENCE TO RELATED APPLICATIONS

This application claims priority from U.S. Provisional Patent Application Ser. No. 60/035,668, filed Jan. 21, 1997 of Tex Yukl for PEOPLE PORTAL SECURITY SYSTEM, the disclosure of which is incorporated herein by reference.

TECHNICAL FIELD

The present invention relates generally to secuility systems and methods. More particularly, it concerns detection of contraband or definedly abnormal objects on persons or personnel and materials or material passing a security checkpoint.

BACKGROUND ART

This invention arises from improvements to apparatus which we previously developed, and from the adaptation of such apparatus to incorporate these improvements. The previously-developed apparatus are the subjects of: U.S. Pat. Nos. 4,234,844, issued Nov. 18, 1980 for "Electromagnetic Noncontacting Measuring Apparatus"; 4,318,108, issued Mar. 2, 1982 for "Bidirectionally Focusing Antenna"; 4,878, 059 issued Oct. 31, 1989 for "Farfield/Nearfield Transmission/Reception Antenna"; 4,947,848, issued Aug. 14, 1990 for "Dielectric-Constant Change Monitoring"; 4,949,094, issued Aug. 14, 1990 for "Nearfield/Farfield Antenna With Parasitic Array"; and 4,975,968, issued Dec. 4, 1990 for "Timed Dielectrometry Surveillance Method and Apparatus". All of these patents are owned in common with the present application, and all are incorporated herein by reference.

There are two primary kinds of contraband detectors presently in use in existing security system. One is a whole body scanner through which people pass and which detects contraband material, such as weapons. The other is a luggage scanner through which material passes for the purpose of detecting contraband, such as bombs. Most such detectors bombard a target with X rays which are safe with material, but which progressively produce damage in the human body over time, and are known to be linked in a causal way to tissue damage that may lead to cancer. Other detectors look for a magnetic anomaly. All such detectors are useful for detecting metals only. These prior art detectors are singularly discriminate in terms of material density, and are indiscriminate in terms of volume. Thus, while they can detect weapons, they cannot detect plastiques or illicit drugs, and they might false-positively indicate that a ring of keys is a weapon. Time-consuming visual screening of captured X ray images, in the case of luggage, greatly slows down security-checkpoint processing of people and their luggage.

Imaging approaches to personnel screening tend to be invasive of a person's privacy and modesty. In other words, screening systems that image the person's body penetrate the person's clothes and highlight the person's physical attributes, effectively undressing the person. Thus, while human body image-reproduction systems, such as X ray systems, may be law-enforcement-friendly, they are traveler-unfriendly to the extent that they constitute an invasion of privacy. Also, and in the case of X ray detecting, such systems constitute a known health hazard.

DISCLOSURE OF THE INVENTION

Briefly, the invented system utilizes an array of microwave transmitter/receivers defining a pail of the perimeter of a portal through which personnel and/or material passes. Generally, the microwave transmitter/receivers are made in accordance with the teachings of the referenced patents. More specifically, they are preferably made in accordance with the priority provisional patent application referenced herein, which are characterized preferably by being spatially, e.g. radially or range-staggered in dual opposing arrays along spaced parallel, e.g. vertical, axes. Also preferably adjacent ones of the transmitter/receiver structures or microwave elements within each array are energized two or more at a time, or most preferably in pair-wise combination. The elements within the array are energized, for illumination of the targeted standing personnel or stationary material, by scanning therearound within an arched portal as in an airport or other secure site, by operatively connected electronics. The interrogated region or volume, whether a standing person or fixed material or the object of interest therein, will be referred to herein as the subject volume, or more simply, the subject.

Preferably, the electronics also monitor and preferably record, e.g. in a memory as a representation thereof in digital form, data characterizing the response of the subject volume to such illumination. Successive time-slice representations of the dielectric constant (propagation) and loss tangent (dissipation) of the region under interrogation of may be derived and may be optionally displayed, as on a display monitor operatively associated with the electronics. A 2-D representation of a 3-D time slice of the subject volume also may be displayed in the form of a modesty-friendly wire-frame image.

Preferably, a discriminator that may take the form of a suitably programmed digital computer or processor that compares the derived dielectric constants with characteristic or baseline dielectric constant ranges stored in a memory determines whether contraband is present in the subject volume and may notify security personnel engaged in monitoring the secure site. Contraband, as used herein, refers to any material within the subject volume constituents of which are determined to be outside predetermined characteristic norms. For a human subject, such norms are physiological norms determined by understanding the normal fluid, tissue and bone constituents of approximately the first two-and-one-half wavelengths $(2.5\lambda)$ of penetration by microwave energy beneath the human subject's skin. For a material subject, such norms are those determined by assumptions regarding the normal constituents of the material within a volume penetrated by the microwave energy. Once the 'normal' contents of the subject volume are determined, then anything more than marginally outside such norms may be defined as contraband, within the broad definition of contraband used herein.

The invention in accordance with its preferred embodiment features a platform with an ingress and egress ramp wherein the platform represents an arched portal in which a person stands immobile while contraband screening takes place. The person's height and weight are measured on the way up the ingress ramp, and the person stands with arms reaching upwardly to grasp a handlebar pre-positioned to the subject's height. An array of antennae mounted within an arched structure is rotated once around the person to collect baseline and other information. Radially inwardly directed pairs of coupled transmitting and receiving antennas arrayed vertically on either side of the platform preferably are constructed in accordance with my U.S. Pat. Nos. 4,878,059 and 4,949,094 respectively entitled "Farfield/Nearfield Transmission/Reception Antenna" and "Nearfield/Farfield Antenna With Parasitic Array".

Antennae driver/receiver electronics are operatively coupled with the antennae arrays to energize the antennae and to measure the dielectric response of the person's body to harmless microwave stimuli preferably in the 5.5 gigaHertz (GHz) range, requiring an antenna having a gain of approximately 14 dbi, an efficiency of approximately 80% and a relatively flat, narrow band-pass, e.g. preferably between 5.0 and 6.0 GHz and more preferably between 5.3 and 5.7 GHz.

A small, high-efficiency antenna is most desirable for use in the present invention in order to minimize the penetration depth-to-range ratio and thus to maximize resulting contrast or signal-to-noise ratio (SNR). In other words, it is desirable to maintain a minimum range between antenna and subject thereby to reduce the distance through the air-as-dielectric space therebetween and to keep each antenna three-dimensionally compact. For these operational reasons, and also in the interest of lightweight and relatively inexpensive system components, antennae with parasitic arrays which are constructed in accordance with above-referenced U.S. Pat. No. 4,949,094 have been found to be most desirable. Those of skill in the art will appreciate, however, that the use of suitable alternatives is contemplated, and is within the spirit and scope of the invention.

An individual's response is compared to a databased baseline response representative of a person of such determined height and weight (or so-called body mass index (BMI)), and peak amplitude and duration excesses over the characteristic baseline are determined to be contraband. In the illustrated application and in accordance with the preferred embodiment of the invention, computer-based imaging system operatively coupled with the electronics uses a generic, wire-frame human body depiction on which anomalous readings that may be indicative of contraband on a human subject standing in the portal is detected, with the contraband being annunciated visually and suitably located on the wire-frame depiction for further manual and/or portable dielectrometer-based searching as is indicated.

These and additional objects and advantages of the present invention will be more readily understood after consideration of the drawings and the detailed description of the preferred embodiment which follows.

DETAILED DESCRIPTION OF THE PREFERRED EMBODIMENT AND BEST MODE OF CARRYING OUT THE INVENTION

Figure 1:
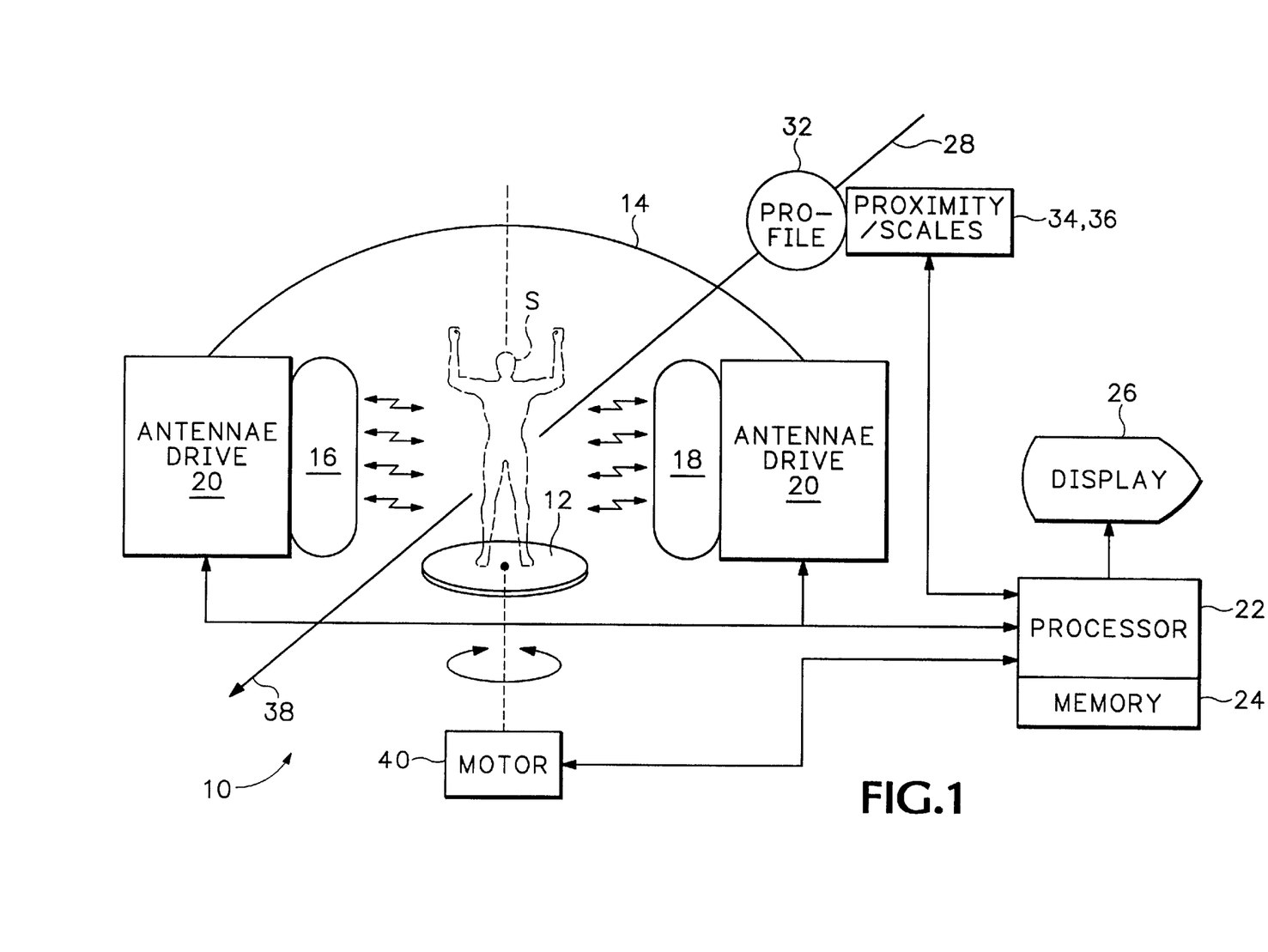
FIG. 1 is a system block diagram of a system made in accordance with the preferred embodiment of the invention.
Figure 2A:
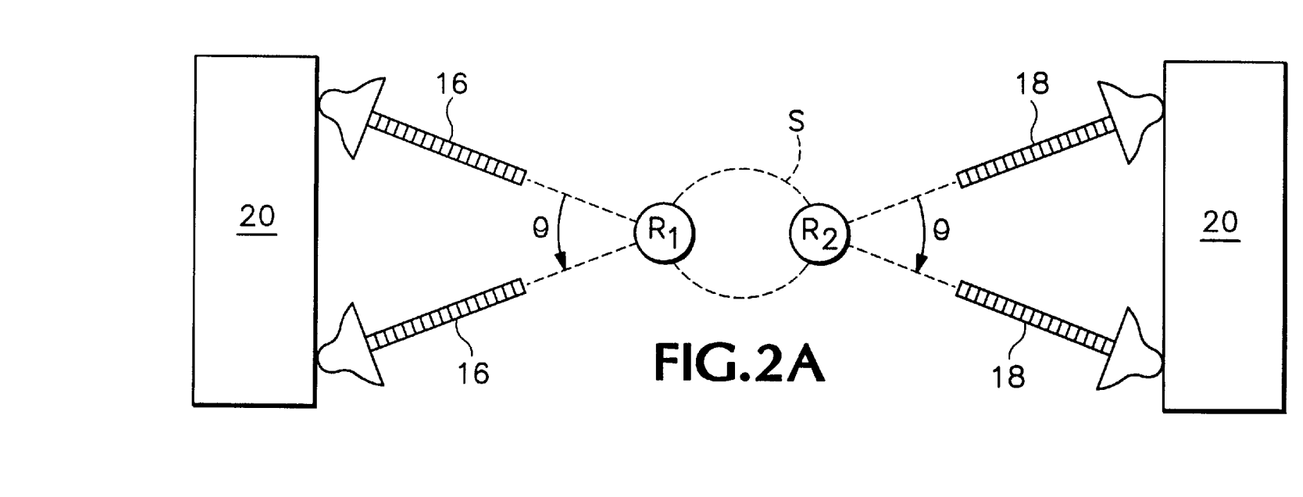
FIGS. 2A and 2B are schematic block diagrams of the transmitter/receiver array and associated electronics in top plan and front elevational views, showing the staggered opposing pairs of microwave antenna elements.
Figure 2B:
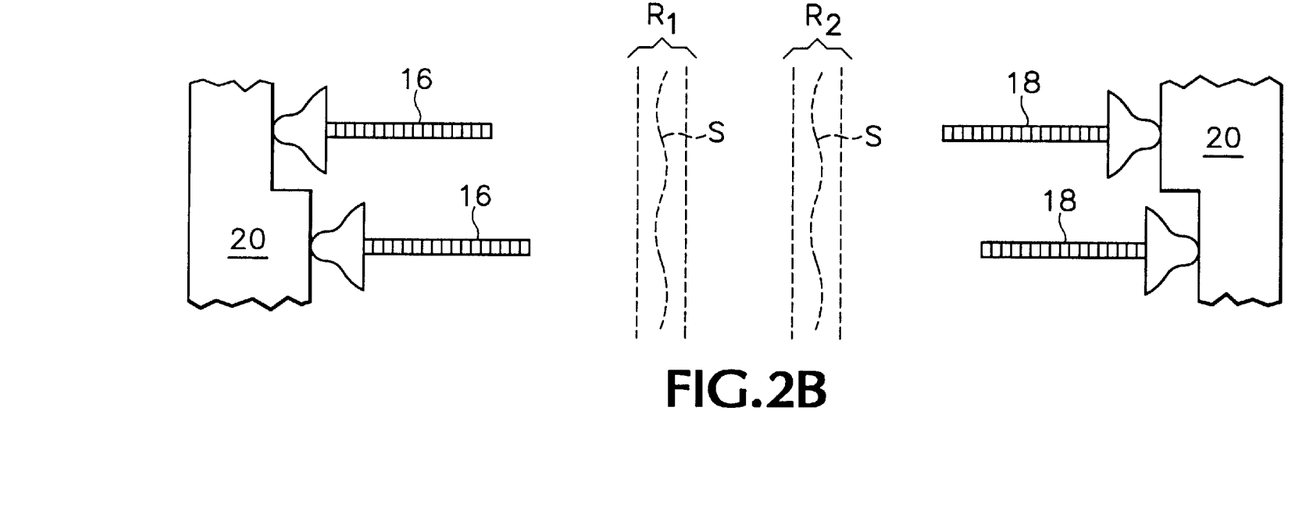
Figure 3:
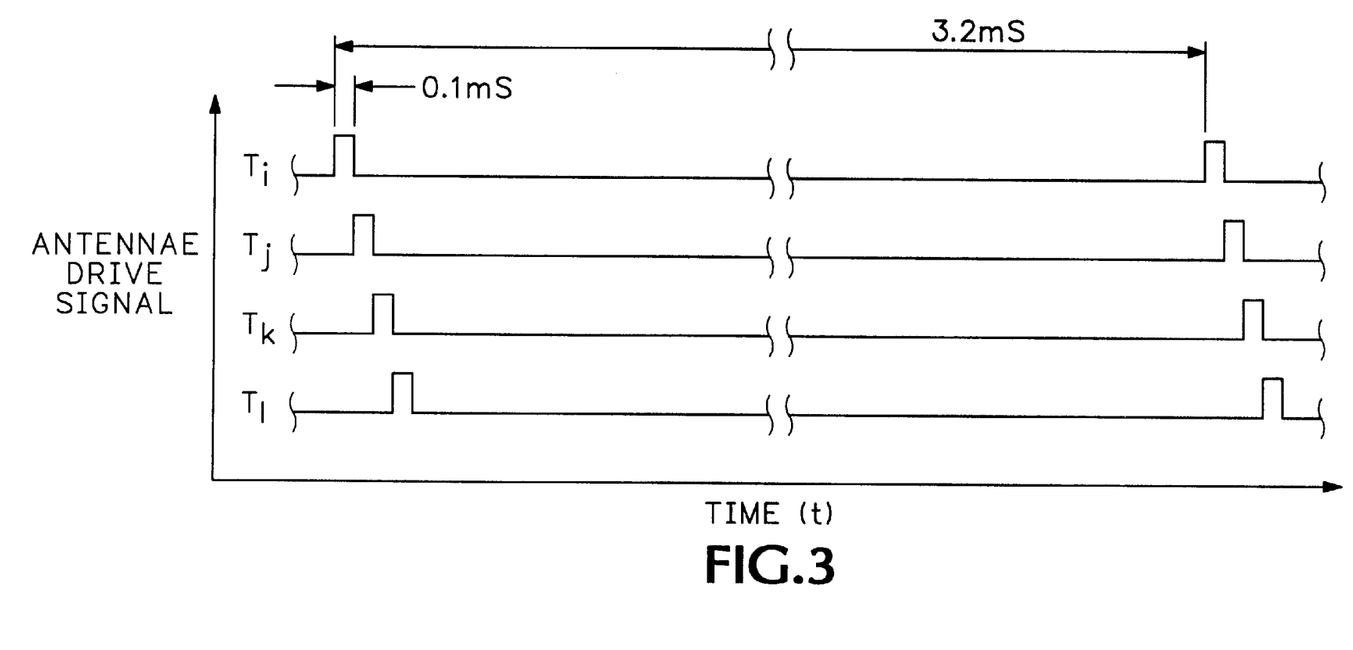
FIG. 3 is a timing diagram illustrating the preferred timing by which the transmitter/receiver structures within the array of FIGS. 1, 2A and 2B are energized.

Referring collectively to FIGS. 1 through 3, it may be seen how the invented system preferably operates to detect and annunciate the presence of anomalous material, e.g. contraband, within the subject volume. It will be understood that any anomalous reading representing a departure from a learned or defined baseline characteristic will be flagged or annunciated, with identification of the region of the anomalous reading relative to the subject volume, but without identification of the type of contraband. Nevertheless, because most weapons and illicit drugs will produce anomalous readings, a knife or plastic explosive or even a small quantity of cocaine, within, on or about a person may be discovered by searching the person in the identified region. Those of skill in the arts will appreciate that FIGS. 1 through 3 are illustrative only of the invented system and are not intended to limit the scope of the present patent in any way.

Those of skill in the arts will appreciate that baseline density measurements may be made of known target materials to profile and characterize their dielectric constant or other pertinent characteristics for positive contraband detection and annunciation. (This approach, which is deemed within the spirit and scope of the invention, is the complement of the preferred approach by which contraband type-undifferentiated readings outside physiological norms are identified as suspect.) Those of skill also will appreciate that lossless targets may be placed, for example, on a human subject, to assist in the establishment of such baselines as may be used for calibration of the invented system and for parameter storage in a memory device within the system's electronics for use by the discriminator described and illustrated herein.

Those of skill in the ails also will appreciate that the use of two or more out-of-phase, elliptically polarized, preferably microwave, transmitters and an interposed receiver ensures constant subject or target illumination that tends to be otherwise obscured by motion artifacts (i.e. the second opposing array is likely to 'see' that to which the first array is 'blind'). Finally, those of skill in the ails will appreciate that cancellation of phase modulation and use of amplitude modulation may facilitate two- or three-dimensional profiling and modeling for contraband detection and annunciation purposes, as such enhance object and edge surface detection. This last feature enables the invented system to distinguish, for example, between a metal implant within a person's body and a characteristically sharp blade and handle profile of a knife or the profile of another weapon such as a gun. The techniques described and illustrated in detail in my U.S. Pat. No. 4,975,968 may be used of those skilled in the art to perform the needed calibrations and measurements for such positive contraband detection as is desired, wherein contraband is intended broadly to cover any material which might otherwise undesirably pass through the portal undetected.

Turning now to FIG. 1, a system block diagram of the invented system is indicated at 10. System 10 preferably includes a generally circular platform 12 for a subject S or personnel to stand on while being screened for contraband, an arched portal 14 including one or more antennae arrays such as arrays 16, 18, with portal 14 being rotatable about a central axis A (see particularly FIG. 4) of platform 12, antennae arrays 16, 18 being operatively coupled with associated antennae drive and timing electronics (ANTENNAE DRIVE) indicated at 20 and a processor 22. Preferably, processor 22 includes a memory 24 at least a portion of which is non-volatile and a suitable display 26 which is preferably a high-resolution color monitor.

In accordance with the preferred embodiment of the invention, system 10 preferably also includes an ingress region indicated generally at 28, ingress region 28 preferably including a ramp 30 (refer briefly to FIGS. 4 and 5) and a profile station 32 operatively connected with processor 22 for determining the approximate height and weight of the screening subject. Profile station 32 may profile the subject by any suitable means such as a proximity detector 34 for measuring the subject's height (the measurement technique being conventional, e.g. timing a reflected sonar, infrared (IR) or laser beam off the subject's head and determining height based on such timing) and a digital scales 36 for measuring the subject's weight (the measurement also being conventional). Those of skill in the arts will appreciate that an individual subject's height and weight are needed to account for variations thereof from expected human body characteristics or norms stored preferably in the non-volatile portion of memory 24. Optionally, system 10 also may include an egress region indicated generally at 38.

In accordance with the preferred embodiment of the invention, system 10 categorizes subjects such as subject S into one of thirty-two categories, i.e. four height classes, four weight classes and two sex classes. It is believed that such weight, height and sex criteria adequately establish a suitable body mass index (BMI) profile against which an individual subject S accurately may be compared to establish when the subject's measured dielectric profile exceeds the human population's norm thus indicating a high degree of probability that the subject is carrying contraband. Those skilled in the arts will appreciate that other baseline factors may be considered, or may be otherwise classified or may be classified into more or fewer physiological categories for comparison with a particular subject S undergoing screening, all within the spirit and scope of the invention.

Turning next to FIGS. 2A and 2B, it may be seen that antennae arrays 16, 18 preferably include plural, e.g. thirty-two, transmitter/receiver antennae pairs in a unique radially inwardly extending orientation from either side of arched portal 14 toward a test subject S. Preferably, each antennae pair is made in accordance with the teachings of my above-referenced U.S. Pat. No. 4,949,094, as suggested by schematic FIGS. 2A and 2B. Electronics 20 are indicated as being operatively and physically relatively closely coupled with each antenna within the plural pairs of antennae 16, 18, as will be understood by those of skill in the arts. From FIG. 2A, it may be seen that the axes of transmitter and corresponding receiver pairs of antennae within arrays 14 and 16 are configured, and the arrays themselves are laterally spaced, as shown, to subtend an angle θ therebetween, thus forming two regions $R_1$, $R_2$ as illustrated, corresponding generally with either side of the subject S, these regions being characterized by higher sensitivity to microwave radiation from the uniquely configured antennae arrays 16, 18. From FIG. 2B, it may be seen that vertically adjacent antennae in each array 16, 18 are axially displaced a few inches, or range-staggered in opposition, thereby effectively enhancing the vertical spatial resolution of system 10. It will be appreciated that an anomaly representing a foreign object on subject S that might be obscured from the 'view' of antennae array 16, nevertheless is more likely to be 'seen' by complementarily range staggered antennae array 18, as will now be described.

It will be appreciated that antennae arrays 16, 18 generally oppose one another diametrically relative to axis A of circular platform 12. Moreover, it may be seen from FIG. 2 that electronics 20 are driven in timed response to drive signals produced by processor 22 to be in synchronism with rotation of platform 12 by any suitable rotary drive means or mechanism such as a servo motor 40 (FIG. 1) controlled also by processor 22. Those skilled in the art will appreciate that relative rotation between platform 12 and portal 14 may be achieved either by rotating platform 12 or portal 14, or both, all within the spirit and scope of the invention.

Preferably, alternate antennae within each allay 16, 18 are axially, or radially, range-staggered as illustrated thereby to increase the sensitivity of system 10 to anomaly detection. This sensitivity increase is achieved, as will be understood by those of skilled in the arts, by effectively transmitting and receiving two microwave energy fronts approximately 2" apart that confront the surface of the body of subject S. Preferably, adjacent antennae within each of arrays 16, 18 are vertically spaced approximately 8" apart such that the opposing allays define therebetween an effective vertical resolution of approximately 4". This effective enhancement of the vertical resolution of system 10 is due to the complementary and opposing, radially staggered configuration of antennae arrays 16, 18 best illustrated in FIG. 2B.

In accordance with the preferred method of the invention, one complete rotation of portal 14 is performed to screen each subject volume such as human subject S. Rotation may be clockwise or counter-clockwise relative to rotational axis A (as seen by brief reference to FIGS. 7A and 7B). Rotation of portal 14 around subject S is controlled by processor 22, and data correlation preferably is performed by processor 22 effectively to sum or average and otherwise normalize the rotation-produced dielectric profiles as between antennae array 16 and antennae allay 18 for comparison with baseline data representative of an at-large population. Counter-rotation between successive screenings effectively unwinds the 'umbilical' that extends over the curved arch or arched portal 14, the 'umbilical' operatively, e.g. electrically, interconnecting antennae arrays 16, 18 on either side thereof and their associated drive and timing electronics 20.

Referring very briefly now to FIG. 3, the transmitting/receiving antennae drive electronics timing is shown. It may be seen that for each transmitter/receiver antenna pair within arrays 16, 18 (timing diagrams for only four adjacent ones of which are shown in FIG. 3), the drive signal preferably has an approximately 3.2 millisecond (ms) period (in accordance with the preferred embodiment described and illustrated herein wherein antennae allays 16, 18 include thirty-two antennae in all) and an approximately 0.1 ms on-time for each vertical scan, thereby producing a relatively low duty cycle on each antenna in the antennae arrays. The angular sample period in which all thirty-two antennae in arrays 16, 18 are sequentially, preferably pair-wise energized and the dielectric response therein monitored preferably represents a 2° arc of the circle through which portal 14 rotates, which period corresponds generally with a human subject of nominal chest size to produce an approximately equilateral cube defining the 3-D spatial resolution of system 10.

Importantly, and in order to optimally illuminate a subject within the interrogation region defined by portal 14 and to detect anomalous readings therefrom, vertically adjacent antennae within each of the antennae arrays 16, 18 are driven at once for approximately twice the duration of the drive timing pulses shown in FIG. 3. For example, vertically adjacent antennae $16_i$ and $16_j$ are driven by a stretched version of drive pulse $T_i$, then antennae $16_j$ and $16_k$ are driven simultaneously by a stretched version of drive pulse $T_j$, then antennae $16_k$ and $16_l$ are driven simultaneously by a stretched version of drive pulse $T_k$, then antennae $16_l$ and $16_m$ are driven simultaneously by a stretched version of drive pulse $T_l$, and so on through all sixteen antennae within array 16 and continuing on in the same direction through all sixteen antennae within array 18. In this way, a foreign object representing contraband on subject S which is tilted upwardly or downwardly relative to the radiation plane defined by a transmitter/receiver antenna pair (refer briefly to FIG. 2B) nevertheless is 'seen' by the antennae array.

In accordance with the preferred embodiment of the invention, 180 samples are read by processor 22 per rotation of portal 14. Those of skill in the arts will appreciate that, within the spirit and scope of the invention, any number of samples, whether angular or vertical and any suitable timing and timebase resolution may be used in screening a subject for contraband.

Figure 4:
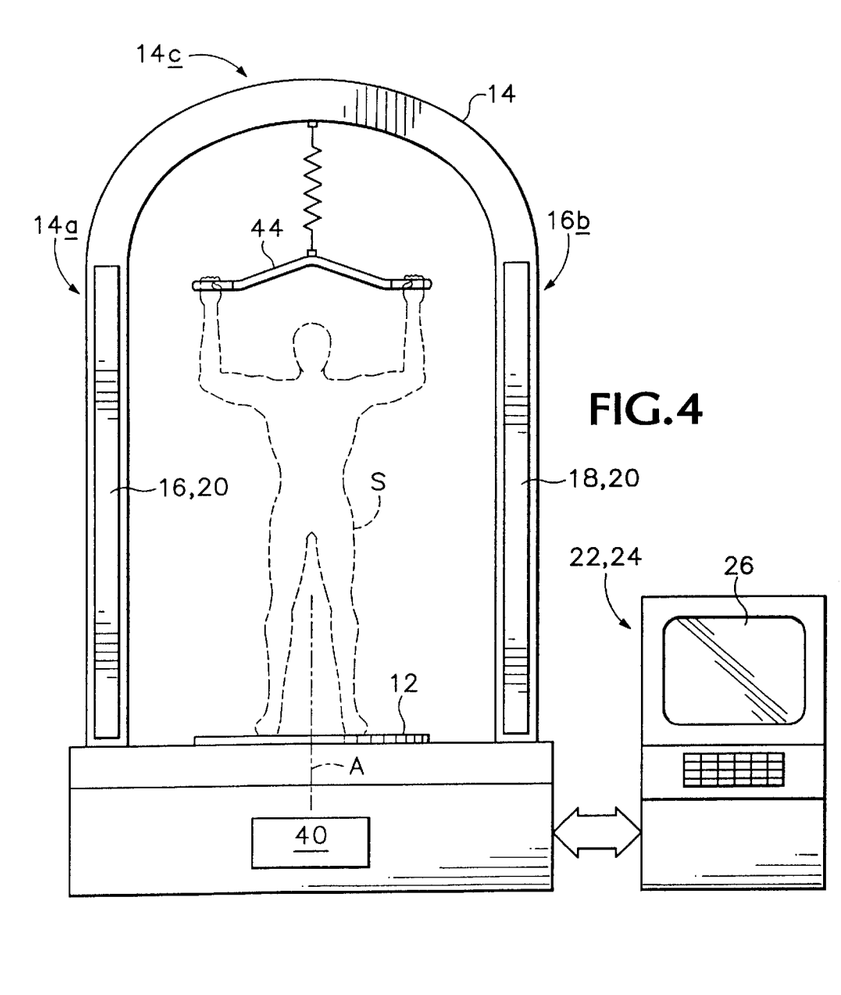
FIG. 4 shows a front elevation of the platform and rotary, arched antennae portal that form a part of the invention.
Figure 5:
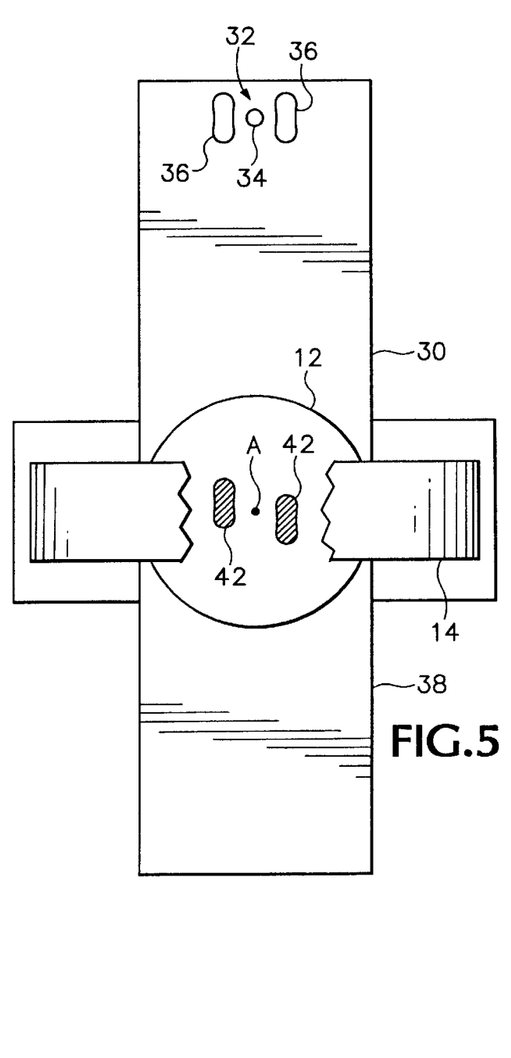
FIG. 5 shows a top plan view of the platform illustrated in FIG. 4.

FIGS. 4 and 5 show portal 14 and platform 12 in front elevational and cutaway top plan view, respectively. FIG. 4 illustrates how arched portal 14 extends upwardly in left and right generally vertical columns 14a and 14b on either side of typically fully clothed subject S (indicated only in general outline), and preferably provides a handlebar 44 in an arched, central, overhead region 14c thereof to be grasped by the subject's two hands in order to extend the subject's arms upwardly clear of the subject's torso. It will be appreciated that the height measurement described above as being made by proximity detector 34 may be used by processor 22 to adjust the height of handlebar 44 above platform 12, thereby to ensure that the subject's arms are stretched sufficiently upwardly for relatively unobstructed illumination of the subject's body—including either side of the torso and the underarms—by antennae arrays 16, 18 but without discomfort to subject S.

FIG. 4 illustrates that, for safety and aesthetic reasons, preferably arched portal 14 is encased in any suitably durable and preferably lightweight material, e.g. molded polymer panels, that protect antennae arlays 16, 18 and electronics 20 from subject S and environmental forces such as airborne particulate and that protect subject S from incidental contact therewith. Those of skill in the arts will appreciate that platform 12, portal 14 and ramp 30 may be of any suitably durable, e.g. conventional, construction and material.

FIG. 5 shows a footprint pattern 42 on platform 12 that guides placement of the feet of subject S for optimal contraband screening. It will be appreciated that staggering the left and right feet by as little as a few inches during rotation of portal 14, a placement suggested by the left and right footprints of pattern 42 better illuminates the insides of the subject's legs and especially the thighs and crotch, thereby reducing the likelihood of undetected contraband hidden therearound. It will also be appreciated that providing footprints on platform 12 for subject S on which to position his or her feet ensures proper central positioning of the subject's body for maximum screening sensitivity and safety as arched portal 14 rotates around the subject.

Figure 6A:
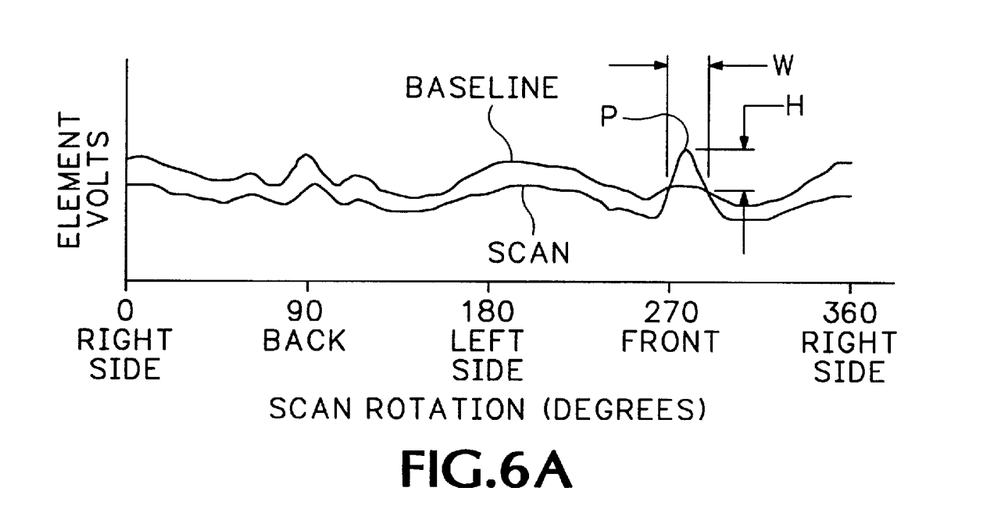
FIG. 6 shows superimposed baseline and instant measurements of dielectric response of the invented system to human bodies standing on the platform.
Figure 6B:
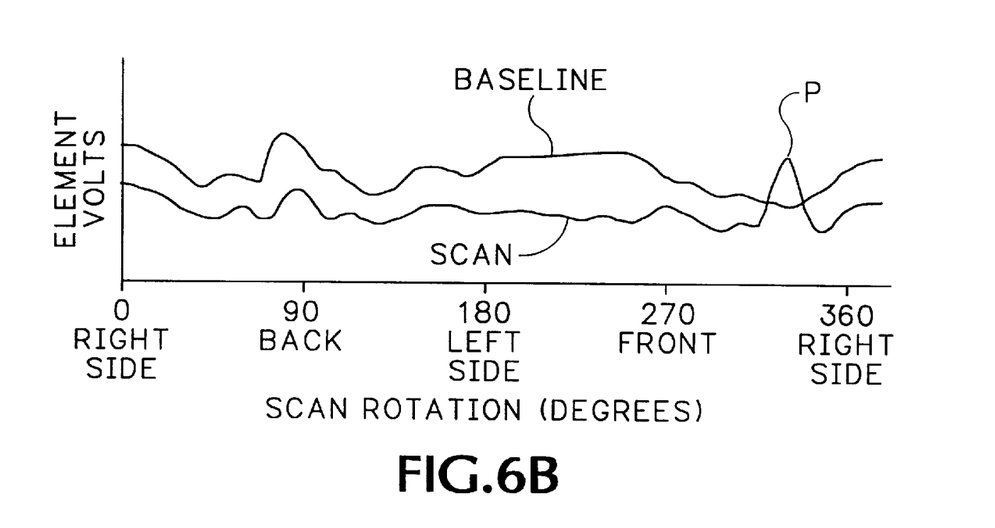

FIGS. 6A and 6B each show superimposed dielectric baseline and response waveforms representative of microwave energy amplitude from antennae arrays 16, 18 incident on a clothed human subject standing on platform 12. All waveforms represent signal amplitude (ELEMENT VOLTS) along the ordinate and rotational angle along the abscissa. A trace labeled BASELINE in each of FIGS. 6A and 6B represents a human body characteristic amplitude waveform that is effectively learned by the computerized system over time. Preferably, such learning involves selective substitution of a peak amplitude in the waveform upon a higher measurement for a particular individual in a given time slot, although within the spirit and scope of the invention averaging or other methods may be used to establish and maintain the characteristic baseline waveform.

Another trace labeled SCAN in each of FIGS. 6A and 6B represents actual measured amplitudes for a particular fictional individual having a contraband target underneath or within the individual's clothing. It may be seen at P in each of FIGS. 6A and 6B that there is a strong peak in measured amplitude representing an anomalous reading or perhaps indicating the presence of contraband on or near the individual at the height of the illustrated set of antennae. In FIG. 6A, this anomalous reading is at nearly 270° and in FIG. 6B this anomalous reading is at nearly 360° through a rotation of portal 14 the starting point of which is at the subject's right side. These elevational and timebased location data are derived from which antennae pair received the high-amplitude and long-duration signal response and when such occurred relative to rotation of platform 12, and may be selected for viewing by security personnel as by clicking on an icon or other push-button provided by processor 22 as part of a preferably graphic user interface (GUI) on display 26. Those of skill in the art will appreciate that such peaks P flagged by invented system 10 may be evaluated by determined threshold criteria such as amplitude (labeled H for height in FIG. 6A) and duration (labeled W for width in FIG. 6A), such that only nominal excursions are not flagged while excursions of significance are flagged as indications of anomalous readings.

It will be understood that typically there are stored in memory associated with processor 22 n such waveforms for each tested subject, where n is the number of antennae pairs in one lateral allay, e.g. sixteen in accordance with the preferred embodiment of the invention. The computer interface permits any and all such waveforms to be displayed by scrolling, although of course it will be appreciated that those waveforms of interest are those in which a peak measured amplitude exceeds a defined threshold determined, preferably, at least in part by characteristic baseline measurements that are learned over time such that they represent the largest possible segment of the population.

Finally, it will be appreciated that the waveform data is interpreted based upon the individual's height, i.e. the individual measurements are stretched or contracted vertically, effectively, to normalize their spread to the height-differentiated baseline spread. In this way, an individual height-influenced dielectric response is comprehended by comparing it to a corresponding one of the stored, weight-categorized 'models' or characteristic baseline responses. If such normalization were not performed by software in accordance with the preferred embodiment of the invention, a shorter individual's lower spine—which tends to reflect a relatively high response—might be mistaken for an anomalous response at the level of the individual's pelvis, which reflects a relatively low response. In this way, false-positives are largely avoided while sensitivity is maximized.

It also will be understood that vertical spatial resolution is governed by n as well as by whether there are one or more such lateral arrays, with two arrays being preferably as described above to enhance the vertical spatial resolution. The time resolution will be understood to be determined by the angular rate of rotation of platform 12, which rate is practically limited by throughput requirements. Throughput of course is the inverse of the maximum allowable scan time per subject volume, which preferably does not exceed 3.5 seconds.

Figure 7A:
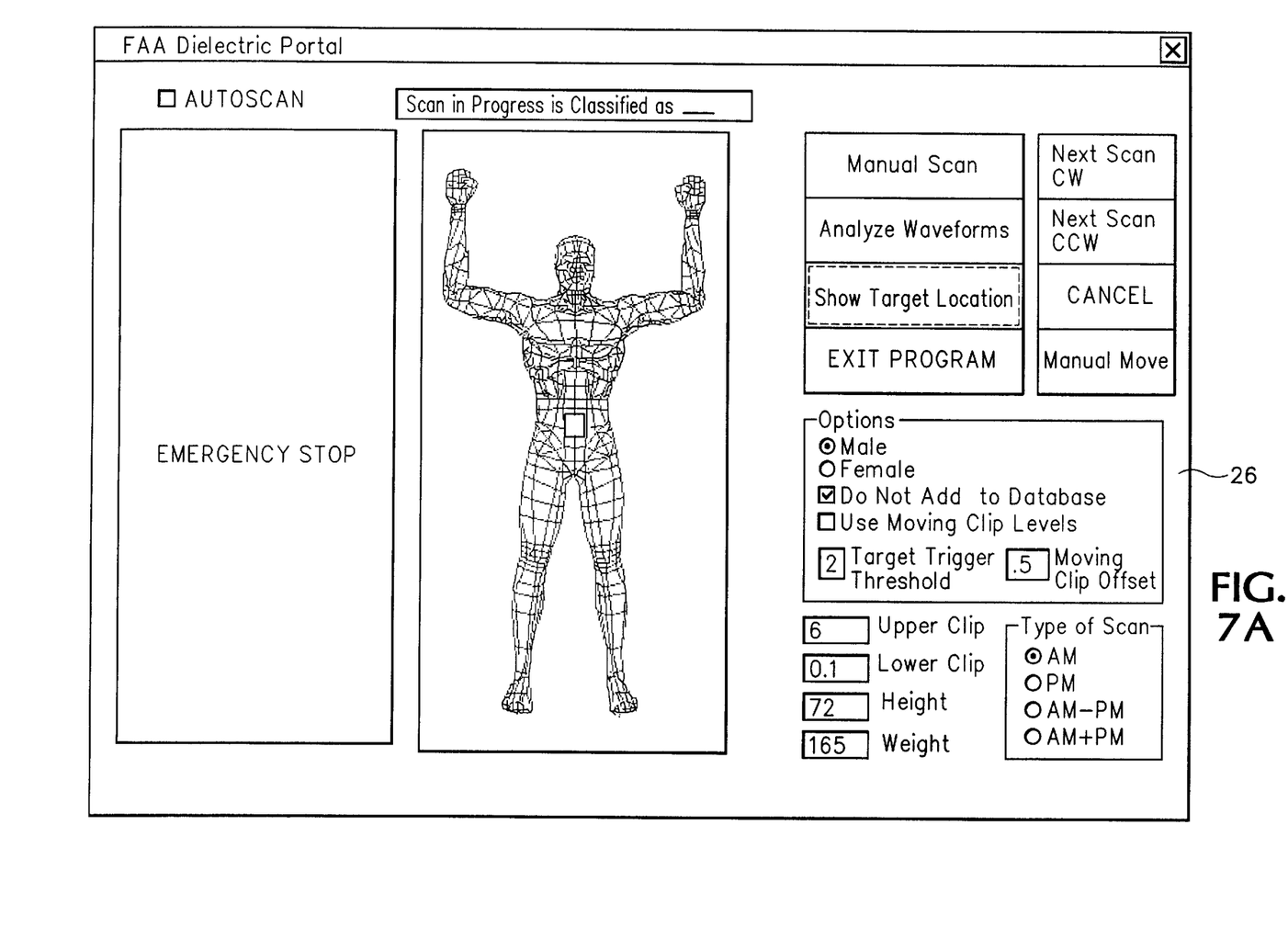
FIGS. 7A and 7B show two different computer display screens illustrating contraband detection and annunciation in accordance with the preferred embodiment of the invented system, with FIG. 7A showing a wire-frame figure with contraband in a first rotational orientation and with FIG. 7B showing the same figure in a second rotational orientation thereto.
Figure 7B:
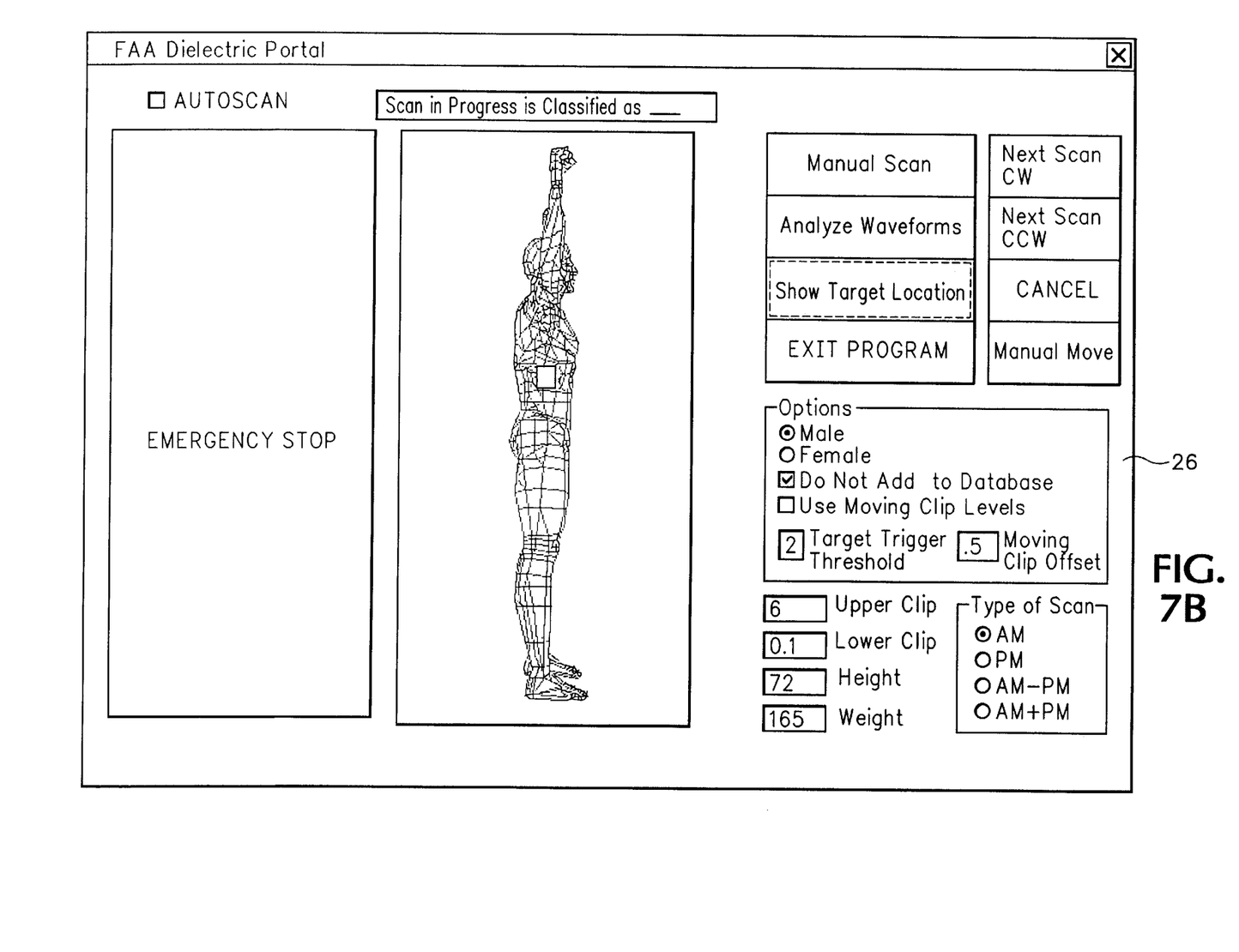

Turning now to FIGS. 7A and 7B, which correspond respectively with FIGS. 6A and 6B, detection of contraband on a subject is illustrated. It may be seen from FIGS. 7A and 7B that two human subjects each illustrated by a generic wire-frame human figure are shown in elevational views corresponding to the rotational angle at which the depicted anomaly is most 'visible.' It will be appreciated that the novel use of generic wire-frame depictions of the human figure avoids the privacy-invasive, immodest suggestions of individual physical characteristics of human subjects that are typical of prior art screening systems.

FIG. 7A annunciates a detected anomaly preferably by a high-contrast visual graphic such as a distinctive rectilinear block (monochrome in the present drawings due to graphic art constraints but preferably by high-contrast color in accordance with the preferred embodiment of the invention) located at the subject's navel. FIG. 7B similarly annunciates a detected anomaly located below the subject's lower right rib. Contrasting FIGS. 7A and 7B, it may be seen that in accordance with the preferred embodiment of the invention anomalous readings that may indicate the presence in the subject volume of contraband are generally centered left to right within a profile of a rotated, generic wire-frame human form. Either of the two illustrated screens selected from various viewing options by clicking on an icon or push-button would inform security personnel monitoring display 26 of the high likelihood of contraband being found in the indicated region within, on or around the subjects' persons, e.g. their attire.

FIGS. 7A and 7B may be appreciated as illustrating other preferred features of the invented method and system 10 whereby the GUI provides security personnel a number of options. These may be seen to include a status window (EMERGENCY STOP), a push-button allay that permits manual scanning, waveform analysis, target location illustration (as is featured in FIGS. 7A and 7B), program exit, clockwise or counter-clockwise scanning, cancellation of a scan and manual moving. They also may be seen to include a number of selectable options including whether a male or female is scanned, whether a particular scan is added to the baseline database, whether moving clip levels are used and which type of scan is used (amplitude modulation (AM) v. phase modulation (PM) or arithmetic combinations thereof). Finally, the GUI preferably permits user selection and/or display of target trigger threshold, moving clip offset, upper and lower clip limits and subject height and weight.

Those of skill in the art will appreciate that, while a graphic display indicating the actual location of the anomalous reading relative to the subject is desirable, nevertheless alternative forms of annunciation or other security measure are envisioned, e.g. an audible or silent alarm may 'sound', a surveillance camera may focus on the subject's further movements within the secured area, egress of subject S from platform 12 may be blocked, etc. All such remedial actions, however light- or heavy-handed, are contemplated and are within the spirit and scope of the invention.

It has been demonstrated by the use of the invention made in accordance with its preferred embodiment that unprecedented versatility and accuracy may be achieved in screening a subject for contraband, yet in keeping with safety and other regulatory, sensitivity, privacy and throughput goals. For example, system 10 constructed in accordance with the preferred embodiment described and illustrated herein— when adjusted not to exceed a false-positive indication level of only 5%—nevertheless achieves a true-positive detection accuracy of approximately 95% for metal targets, 90% for ceramics, 70% for polystyrene, 60% for synthetic plastique and 55% for synthetic drugs. It is noted that these last four target contraband categories very effectively detected in accordance with the invention heretofore have proven to be virtually undetectable with human subject screening and often have proven to be undetectable even with invasive X ray detection schemes.

Importantly, no combination of such metal, ceramic, polystyrene, plastique or drug targets is predictably undetected despite the less-than-perfect sensitivity of invented system 10. Instead, any likelihood of missing the above-listed and other non-physiological objects during a physiological screen of a human subject is so low and unpredictable that it cannot be counted on. In other words, there is believed to be no combination of the above-described contraband contents of subject volume that one may reasonably expect to be screened by invented system 10 without discovery. Accordingly, although system 10's extremely high sensitivity is not infinite, nevertheless it is sufficiently high to deter even the most careful or ingenious attempt to elude its detection capability.

Those of skill in the art will appreciate that a conveyor may be included as a part of the invented system for moving personnel or material through such a portal as is described. In such a way, material or personnel that are otherwise immobile may be moved into relatively fixed position and screened for contraband within the rotational platform/portal construction, yet with all of the advantages of the invention in its preferred embodiment described herein. Such conveyor may be of any suitable design, as by effectively replacing the ingress and egress regions described and illustrated herein of the preferred embodiment, in accordance with the teachings of my above-referenced U.S. Pat. No. 4,975,968.

The invention now may be understood in light of the invented system described above also to involve a dielectrometric method for screening a human subject, whether for contraband in the classic sense of something illicit or illegal or whether simply for a physiological abnormality. The invented steps preferably include 1) providing an interrogation region within which the subject reposes, e.g. platform 12 and portal 14; 2) illuminating the subject within the interrogation region with microwave energy from an allay of plural transmitter/receiver antennae and monitoring the dielectric response therefrom, e.g. via the use of antennae arrays 16, 18; 3) comparing the dielectric response with baseline physiological response data stored in memory to produce data representative of any difference therebetween; and 4) evaluating such data by use of defined screening criteria, with the last two numbered steps preferably being performed by a suitably programmed computer, e.g. a conventional digitizer, processor 22 and memory 24 being used for digital data storage preferably in a multi-dimensional array. Thus, it may be seen that the method does not require that the human subject be standing, only that the subject preferably be in relatively calm repose so that motion artifacts are avoided. Those of skill in the art will appreciate that myriad physiological screening criteria may be used in such a method.

Preferably, after the irradiating and before the comparing steps, the method further includes digitizing and storing the result of the monitoring in a memory. Also preferably, the irradiating-and-monitoring step is performed by relatively rotating a generally planar perimetric antennae array, e.g. portal 14 including antennae arrays 16, 18, and a base, e.g. platform 12, supporting the subject in repose about an axis, e.g axis A which need not be vertical within the spirit and scope of the invention, generally aligned with the subject.

Accordingly, while the present invention has been shown and described with reference to the foregoing preferred system, it will be apparent to those skilled in the art that other changes in form and detail may be made therein without departing from the spirit and scope of the invention as defined in the appended claims.

I claim:

1. A security system for contraband detection comprising:
   a portal defining an interrogation region therewithin into which region a screening target may be introduced;
   a transmitter/receiver array mounted in a defined at least partial perimeter around said region for illuminating the target by a first microwave beam and for monitoring the dielectric response to said first microwave beam to produce a dielectric response signal representative of the dielectric response of the target to microwave illumination; and electronics operatively connected with said transmitter/receiver array for energizing said array in accordance with defined microwave energy amplitude and timing characteristics and for monitoring said dielectric response signal, said electronics including a discriminator for comparing said dielectric response signal with a defined characteristic response signal, said electronics producing an indication of a difference therebetween meeting predefined criteria.

2. The system of claim 1, wherein said transmitter/receiver array includes plural transmitter/receiver structures arrayed in an opposing, staggered spatial relationship with one another that defines at least a part of said portal.

3. The system of claim 2, wherein ones of said plural transmitter/receiver structures are energized by said electronics in pair-wise combination for concurrent illumination by said ones of the target for a first defined period of time and wherein other ones of said plural transmitter/receiver structures are energized by said electronics also in pair-wise combination for concurrent illumination by said other ones of the target for a second defined period of time that is substantially different from said first defined period of time.

4. The system of claim 2, wherein said transmitter/receiver array includes an elliptically polarized microwave energy source.

5. The system of claim 1 which further comprises an annunciator operatively connected with said discriminator for notifying security personnel of such indication.

6. The system of claim 5, wherein said annunicator includes a display monitor for indicating within the target the physical location therein corresponding with the indicated difference.

7. The system of claim 6 in which the target is a human subject, wherein said display monitor includes a depiction of a generic human form and wherein the physical location is indicated by a high-contrast graphic feature superimposed on said depiction.

8. The system of claim 1 which further includes a platform beneath said portal for supporting the target within said interrogation region, wherein said portal and said platform are rotatable relative to one another for illumination of said interrogation region from substantially all sides by said transmitter/receiver array.

9. The system of claim 1, wherein said electronics include a digitizer for the monitoring, a digital memory for buffering and a digital processor for the comparing and wherein the dielectric response of the target to the illumination is derived by said electronics, wherein said digital memory includes stored contraband dielectric constant parameters used by said discriminator for comparison thereof with the derived dielectric constant of the target.

10. The system of claim 9 which further comprises an annunciator for indicating the derived dielectric constant of the target, wherein said processor produces an indication of said derived dielectric constant for notifying by said annunciator.

11. A security system for contraband detection comprising:

a platform on which personnel may stand;

a rotary drive mechanism adjacent said platform;

a portal adjacent said platform and extending upwardly therefrom, said portal and said platform being rotatable by said rotary drive mechanism relative to one another, said portal including generally vertical upward extents each having antennae arrays therein operative to illuminate such personnel standing on said platform with microwave energy and to measure the dielectric response of such personnel to said illumination to produce a response signal representative of such dielectric response during relative rotation of said portal and said platform; and a processor for time-correlating said response signal with the relative rotation of said portal and said platform to produce spatio-temporal data indicative of the dielectric response of such personnel to such illumination, said processor further for comparing such data to previously stored baseline data and for annunciating any differences therebetween which meet predefined criteria indicating the presence of contraband adjacent such personnel.

12. The system of claim 11 which further comprises a display monitor for illustrating the physical location relative such personnel of the presence of contraband.

13. The system of claim 12 which further comprises a personnel body height measurement subsystem operatively connected with said processor for compensating for such personnel's height during such comparing.

14. The system of claim 13 which further comprises a personnel body weight measurement subsystem operatively connected with said processor for compensating for such personnel's weight during such comparing.

15. The system of claim 11, wherein said antennae arrays are operative to illuminate such personnel with microwave energy in a frequency range between approximately 5 and 6 gigaHertz.

16. The system of claim 15, wherein said antennae arrays are operative to illuminate such personnel with microwave energy in a frequency range between approximately 5.3 and 5.7 gigaHertz.

17. The system of claim 16, wherein said antennae arrays are operative to illuminate such personnel with microwave energy at a frequency of approximately 5.5 gigaHertz.

18. A dielectrometric method for screening a human subject comprising:

providing an interrogation region within which the subject reposes;

illuminating the subject within the interrogation region with microwave energy from an array of plural transmitter/receiver antennae and monitoring the dielectric response therefrom;

comparing the dielectric response with baseline physiological response data stored in memory to produce data representative of any difference therebetween; and evaluating such data by use of defined screening criteria.

19. The method of claim 18 which further comprises, after said illuminating-and-monitoring and before said comparing steps, digitizing and storing such result of said monitoring in a memory.

20. The method of claim 18, wherein said illuminating-and-monitoring step is performed by relatively rotating a generally planar perimetric antennae array and a base supporting the subject in repose about an axis generally aligned with the subject.

* * * * *